(12) United States Patent
Salkola et al.

(10) Patent No.: US 12,295,883 B2
(45) Date of Patent: May 13, 2025

(54) APPARATUS AND SYSTEM FOR ADMINISTERING DRUGS ONTO OCULAR SURFACE

(71) Applicant: ICARE FINLAND OY, Vantaa (FI)

(72) Inventors: Mika Salkola, Espoo (FI); Juha Päällysaho, Vantaa (FI)

(73) Assignee: ICARE FINLAND OY, Vantaa (FI)

( * ) Notice: Subject to any disclaimer, the term of this patent is extended or adjusted under 35 U.S.C. 154(b) by 0 days.

(21) Appl. No.: 18/245,181

(22) PCT Filed: Sep. 13, 2021

(86) PCT No.: PCT/FI2021/050608
§ 371 (c)(1),
(2) Date: Mar. 14, 2023

(87) PCT Pub. No.: WO2022/058652
PCT Pub. Date: Mar. 24, 2022

(65) Prior Publication Data
US 2023/0355435 A1    Nov. 9, 2023

(30) Foreign Application Priority Data
Sep. 18, 2020   (FI) ..................................... 20205905

(51) Int. Cl.
*A61F 9/00*        (2006.01)
*A61F 9/007*       (2006.01)

(52) U.S. Cl.
CPC ........ *A61F 9/0026* (2013.01); *A61F 9/00781* (2013.01)

(58) Field of Classification Search
CPC ........ A61F 9/0026; A61F 9/0008; A61B 3/16; A61B 3/165
See application file for complete search history.

(56) References Cited

U.S. PATENT DOCUMENTS

| 3,308,653 A | 3/1967 | Wilfred |
| 6,869,421 B2 * | 3/2005 | Hanley ................ A61F 9/0008 604/300 |

(Continued)

FOREIGN PATENT DOCUMENTS

| WO | WO-9606560 A1 * | 3/1996 | ............... A61B 3/16 |
| WO | WO-2019211217 A1 * | 11/2019 | ........... A61B 3/0033 |

(Continued)

OTHER PUBLICATIONS

European Patent Office, Notification of Transmittal of the International Preliminary Report on Patentability, International Application No. PCT/FI2021/050608, mailed Nov. 30, 2022, 14 pages.

(Continued)

*Primary Examiner* — Sarah Al Hashimi
*Assistant Examiner* — Arjuna P Chatrathi
(74) *Attorney, Agent, or Firm* — Ziegler IP Law Group, LLC.

(57) ABSTRACT

An apparatus for administering a drug onto an ocular surface of a subject, the apparatus including a probe holding means for holding a probe within the apparatus. The probe has a first part being made of a bio-compatible material, and a second part being made of a magnetic material, the first part having a proximal end connected to the second part and a distal end opposite to the proximal end, wherein the distal end of the first part is employed to carry the drug. The apparatus also has an induction coil and control circuit, wherein the control circuit controls the induction coil to produce a first magnetic force and a second magnetic force, in an alternating manner, to release the probe in a first direction and to retract the probe in a second direction, respectively, wherein, when released in the first direction, the probe administers the drug from the distal end of the first part upon touching the ocular surface of the subject.

9 Claims, 4 Drawing Sheets

(56) References Cited

U.S. PATENT DOCUMENTS

| | | | | |
|---|---|---|---|---|
| 2004/0186373 | A1* | 9/2004 | Dunfield | A45D 34/04 |
| | | | | 424/449 |
| 2005/0137473 | A1* | 6/2005 | Kontiola | A61B 3/16 |
| | | | | 600/398 |
| 2009/0306493 | A1 | 12/2009 | Kontiola | |
| 2011/0087138 | A1* | 4/2011 | Kahook | A61F 9/00781 |
| | | | | 601/89 |
| 2018/0368681 | A1* | 12/2018 | Makkeli | A61B 3/16 |
| 2019/0150736 | A1* | 5/2019 | Wallace | G16H 20/13 |
| 2019/0380577 | A1* | 12/2019 | Martin | A61B 3/0025 |

FOREIGN PATENT DOCUMENTS

| | | | |
|---|---|---|---|
| WO | 2019234292 A1 | 12/2019 | |
| WO | 2020146714 A1 | 7/2020 | |

OTHER PUBLICATIONS

European Patent Office, Notification of Transmittal of the International Search Report and the Written Opinion of the International Searching Authority, or the Declaration, International Application No. PCT/FI2021/050608, mailed Dec. 9, 2021, 15 pages.

Finnish Patent and Registration Office, Search Report, U.S. Appl. No. 20/205,905, dated Jan. 20, 2021, 2 pages.

Wikipedia, Ocular tonometry, [online], Aug. 10, 2020, [retrieved on Jan. 15, 2021]. Retrieved from Section rebound tonometry (clarifies the definition of rebound tonometry), 7 pages.

\* cited by examiner

APPARATUS AND SYSTEM FOR ADMINISTERING DRUGS ONTO OCULAR SURFACE

TECHNICAL FIELD

The present disclosure relates generally to ophthalmic treatment devices, and more specifically, to apparatuses, probes and systems for administering drugs onto an ocular surface of a subject.

BACKGROUND

Eyes are one of the most sensitive parts of human body and require extreme care and precautions. However, even with such extreme care and precautions, eyes tend to suffer a variety of diseases due to various factors such as ageing, pollution, accidental damage, genetic factors and so forth. In such instances, drugs are prescribed by physicians for treatment of diseases such as conjunctivitis, corneal infections, glaucoma, dry-eye and so forth. Generally, for treatment of ocular diseases, drugs are required to be administered directly onto the ocular surface of the eye.

Conventional systems for administering drugs onto the ocular surface include, but are not limited to, vials, injections, or using a finger of the subject to apply ointments. However, systems for self-use are limited mainly to vials for eye drops, wherein administration of drugs using injections or as ointments are generally required to be administered by a trained professional. Furthermore, such conventional systems result in wastage of substantial amount of drugs. Moreover, several eye conditions require a measured dosage of the drugs to be administered directly onto the ocular surface that may be in orders of magnitude ranging from milligrams to micrograms. Additionally, some eye conditions may require administration of drugs on a specific part of the eye, for example the pupil or the corners of the eye. Conventional systems fail to provide a degree of control that allows such precise measurement of dosage of drugs or administration of drugs on the specific part of the eye.

In recent times, the science of ophthalmology and pharmacology has progressed to introduce systems dedicated to deliver the prescribed doses of drugs at the site of target. Such systems include nanotechnology-based drug carriers and electrochemical repulsion-based delivery systems. However, such systems generally, involve complex setup and are uneconomical. Therefore, a trained medical professional such as a doctor, an ophthalmologist, an ophthalmic nurse or an optometrist is required for the setup and operation of such systems. Moreover, such systems may require longer durations of contact with the ocular surface of the eye and may cause grating, dryness, wetting, or itching in the ocular surface.

Therefore, in light of the foregoing discussion, there exists a need to overcome the aforementioned drawbacks associated with conventional techniques for administering drugs onto the ocular surface.

SUMMARY

The present disclosure seeks to provide an apparatus for administering a drug onto an ocular surface of a subject. The present disclosure also seeks to provide a probe for administering drugs onto the ocular surface of the subject. The present disclosure also seeks to provide a system for administering drugs onto the ocular surface of the subject. The present disclosure seeks to provide a solution to the existing problem of imprecise, wasteful, and unsafe administration of drug onto the ocular surfaces. An aim of the present disclosure is to provide a solution that overcomes at least partially the problems encountered in prior art, and provides an accurate, safe, and precise procedure for administering drugs onto the ocular surfaces.

In one aspect, an embodiment of the present disclosure provides an apparatus for administering a drug onto an ocular surface of a subject, the apparatus comprising:
  a probe holding means for holding a probe within the apparatus,
  the probe comprising
    a first part being made of a bio-compatible material, and
    a second part being made of a magnetic material, the first part having a proximal end connected to the second part and a distal end opposite to the proximal end, wherein the distal end of the first part is employed to carry the drug;
  an induction coil and its control circuit, wherein the control circuit is operable to control the induction coil to produce a first magnetic force and a second magnetic force, in an alternating manner, to release the probe in a first direction and to retract the probe in a second direction, respectively, wherein, when released in the first direction, the probe is to administer the drug from the distal end of the first part upon touching the ocular surface of the subject;
  a first sensor that is to be employed to sense a displacement and/or velocity of the probe; and
  a controller configured to:
    collect, from the first sensor, sensor data indicative of the displacement and/or velocity of the probe as a function of time;
    analyse the sensor data to detect whether or not the probe touched the ocular surface during a given instance of release of the probe in the first direction.

In another aspect, an embodiment of the present disclosure provides a probe for administering a drug onto an ocular surface of a subject, the probe comprising:
  a first part made of a bio-compatible material; and
  a second part made of a magnetic material,
wherein the first part has a proximal end connected to the second part and a distal end opposite to the proximal end, and wherein the distal end of the first part is employed to carry the drug; and
at least one capillary tube arranged inside at least the first part of the probe, an opening of the at least one capillary tube being at the distal end of the first part, the at least one capillary tube being filled with the drug.

In yet another aspect, an embodiment of the present disclosure provides a system for administering a drug onto an ocular surface of a subject, the system comprising:
  a probe comprising
    a first part being made of a bio-compatible material, and
    a second part being made of a magnetic material, the first part having a proximal end connected to the second part and a distal end opposite to the proximal end, wherein the distal end of the first part is employed to carry the drug; and
    at least one capillary tube arranged inside at least the first part of the probe, an opening of the at least one capillary tube being at the distal end of the first part, the at least one capillary tube being filled with the drug;
  an apparatus comprising:

probe holding means for holding the probe within the apparatus; and an induction coil and its control circuit, wherein the control circuit is operable to control the induction coil to produce a first magnetic force and a second magnetic force, in an alternating manner, to release the probe in a first direction and to retract the probe in a second direction, respectively, wherein, when released in the first direction, the probe is to administer the drug from the distal end of the first part upon touching the ocular surface of the subject.

Embodiments of the present disclosure substantially eliminate or at least partially address the aforementioned problems in the prior art, and enable a straightforward, safe, and user-friendly procedure for administering drugs onto the ocular surfaces.

Additional aspects, advantages, features, and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides an apparatus for administering a drug onto an ocular surface of a subject, the apparatus comprising:

a probe holding means for holding a probe within the apparatus, the probe comprising
a first part being made of a bio-compatible material, and
a second part being made of a magnetic material, the first part having a proximal end connected to the second part and a distal end opposite to the proximal end, wherein the distal end of the first part is employed to carry the drug;

an induction coil and its control circuit, wherein the control circuit is operable to control the induction coil to produce a first magnetic force and a second magnetic force, in an alternating manner, to release the probe in a first direction and to retract the probe in a second direction, respectively, wherein, when released in the first direction, the probe is to administer the drug from the distal end of the first part upon touching the ocular surface of the subject;

a first sensor that is to be employed to sense a displacement and/or velocity of the probe; and a controller configured to:
collect, from the first sensor, sensor data indicative of the displacement and/or velocity of the probe as a function of time;
analyse the sensor data to detect whether or not the probe touched the ocular surface during a given instance of release of the probe in the first direction.

In another aspect, an embodiment of the present disclosure provides a probe for administering a drug onto an ocular surface of a subject, the probe comprising:

a first part made of a bio-compatible material; and
a second part made of a magnetic material,
wherein the first part has a proximal end connected to the second part and a distal end opposite to the proximal end, and wherein the distal end of the first part is employed to carry the drug; and at least one capillary tube arranged inside at least the first part of the probe, an opening of the at least one capillary tube being at the distal end of the first part, the at least one capillary tube being filled with the drug.

In yet another aspect, an embodiment of the present disclosure provides a system for administering a drug onto an ocular surface of a subject, the system comprising:

a probe comprising
a first part being made of a bio-compatible material, and
a second part being made of a magnetic material, the first part having a proximal end connected to the second part and a distal end opposite to the proximal end, wherein the distal end of the first part is employed to carry the drug; and at least one capillary tube arranged inside at least the first part of the probe, an opening of the at least one capillary tube being at the distal end of the first part, the at least one capillary tube being filled with the drug;

an apparatus comprising:
probe holding means for holding the probe within the apparatus; and
an induction coil and its control circuit, wherein the control circuit is operable to control the induction coil to produce a first magnetic force and a second magnetic force, in an alternating manner, to release the probe in a first direction and to retract the probe in a second direction, respectively, wherein, when released in the first direction, the probe is to administer the drug from the distal end of the first part upon touching the ocular surface of the subject.

The present disclosure provides the apparatus, the probe and the system for administering the drug onto the ocular surface of a subject. The apparatus enables safe and painless contact of the probe with the ocular surface of the subject. In this regard, the part of probe contacting the ocular surface is composed of a bio-compatible material to prevent an unsafe or damaging contact of the probe with the eye. Moreover, the probe is strategically designed to accurately provide an intended amount of the drug onto the ocular surface. Specifically, the probe is capable of providing an amount of drug in orders of magnitudes ranging from milligrams to micrograms. Additionally, beneficially, the apparatus provides hygienic and contamination-free administration of drugs to the ocular surface of the subject. Furthermore, the apparatus and the system provide a high degree of control to a user thereof, allowing targeted operation and administration of the drug onto the specific parts of the ocular surface. Notably, the probe allows delivery of drug in different forms such as liquids, solids (for example, powder or granules), sol. Moreover, the apparatus and the system provide an economical and effortless solution to administration of drugs onto the ocular surface that can be employed by a subject on whom the drug is being administered.

The present disclosure provides an apparatus for administering a drug onto the ocular surface of a subject. Herein, the term "subject" refers to a human or an animal that requires the drug to be administered onto their ocular surface. Notably, the ocular surface refers to a surface of the eye that acts as an interface between the functioning eye and an external environment onto which the drug is administered for treatment of eye-related conditions such as conjunctivitis, corneal infections, glaucoma, dry-eye and so forth. In particular, the ocular surface of the eye forms the barrier between external environment and the eye. The drug administered thereon permeates the ocular surface and acts on the intended part of the eye. Notably, administration of the drug directly onto the ocular surface of the subject enables precise dosing of the drug and substantially eliminates any wastage thereof. It will be appreciated that the administration of the drug onto the ocular surface of the subject can be performed by the subject himself or by another person. Hereinafter, the person operating the apparatus, or the system is referred as a "user", who could be a doctor, an ophthalmologist, an optometrist, an ophthalmic nurse, or other medical personnel.

Throughout the present disclosure, the term "drug" refers to a chemical compound or a substance intended for healing, treating, altering, improving, restoring, relieving, and/or curing a condition or a disease of the eye. The drug includes an active ingredient or combination of active ingredients, optionally infused into an expedient or mixed in a carrier. Notably, the drug may be in form of a liquid, a sol, or a powder. Upon administration of the drug onto the ocular surface, the drug may dissolve in the fluid of the tear film on the ocular surface, adhere to the corneal surface of the eye, or pass through the cornea into the anterior chamber fluid (aqueous humour) of the eye, depending on the type of drug. In an example, the drug may be a Prostaglandin analogue in a liquid form for treatment of glaucoma.

The present disclosure provides a probe. Notably, the probe is an elongate instrument held by the probe holding means of the apparatus. An example of the probe holding means is an opening in an apparatus in which the probe can be inserted. The probe can be held in the opening via magnetic force for example, alternatively the probe can be held with friction in the opening. The opening is preferably tubular and dimensioned to surround at least part of the probe as the probe is inserted in the opening. The probe is designed in a manner to have minimal contact with the ocular surface while administering the drug thereon. The probe is detachably attached to the apparatus to be part of the apparatus. In an instance, the probe may be a single-use disposable unit, that may be discarded after the administration of the drug to ensure hygienic operation. Indeed, when the apparatus is in use the probe is part of the apparatus.

The probe comprises a first part made of a bio-compatible material. In particular, the first part of the probe carries the drug. Therefore, the first part of the probe comes in close contact with the ocular surface of the subject. Beneficially, the first part being made of bio-compatible material enables the probe to function in intimate contact with living tissues of the eye causing minimal discomfort or pain. Notably, the bio-compatible material is free from carcinogenicity, toxicity, and is resistive to corrosion. Examples of bio-compatible materials include, but are not limited to, metallic bio-compatible materials (such as stainless steel, titanium alloys, cobalt alloys), polymeric bio-compatible materials (such as polyethylene, polytetrafluoroethylene), ceramic bio-compatible materials (such as Alumina, Zirconia, Bio-glass).

The probe comprises a second part made of a magnetic material. Notably, the magnetic material enables the probe to be held by the probe holding means. Furthermore, the induction coil is operable to induce motion in the probe by providing a magnetic force to the magnetic material of the second part. In an instance, the magnetic material is a ferromagnetic material (for example, iron, nickel, and the like) used for manufacturing the second part of the probe. It will be appreciated that a momentary and brief contact of the probe with the ocular surface is required to avoid any damage or discomfort to the eye. Therefore, the magnetic material and the magnetic forces provided by the induction coil enable such quick motion of the probe. The second part can form an elongated magnetic body of the probe.

The first part of the probe has a proximal end connected to the second part and a distal end opposite to the proximal end. The distal end of the first part is employed to carry the drug. Notably, the distal end of the first part of probe comes in contact with the ocular surface to administer a given amount of the drug onto it. Herein, the proximal end connected to the second part of the probe is held within the probe holding means, wherein the distal end protrudes from the apparatus to contact the ocular surface for administration of the drug.

In an embodiment, the second part of the probe is an elongate metallic rod, wherein the first part of the probe is implemented as a spherical or ellipsoidal element. Herein, the proximal end and the distal end of the first part are diametrically opposing points on the spherical or ellipsoidal element. Beneficially, such spherical or ellipsoidal element increases surface area of the probe, thereby reducing an impact pressure of the probe on the ocular surface. Furthermore, the spherical or ellipsoidal element enables the first part to provide a larger surface for carrying the drug thereon. Optionally, the size of the probe ranges from 1×10 mm up to 5×40 mm. In an example, the size of probe may have a width (or diameter) in a range of 1, 1.25, 1.5, 1.75, 2, 2.5 or 3 mm up to 2, 2.5, 3, 3.5, 4 or 5 mm and a length in a range of 10, 12.5, 15, 20 or 25 mm up to 15, 20, 25, 30, 35 or 40 mm.

In an embodiment, the probe further comprises at least one capillary tube arranged inside at least the first part of the probe, an opening of the at least one capillary tube being at the distal end of the first part, the at least one capillary tube being filled with the drug. Notably, the at least one capillary tube carries the drug in the liquid or sol form. Herein, the at least one capillary tube may carry multiple doses of drug therein and a predetermined amount of the drug may be administered from the opening of the capillary tube onto the ocular surface when the distal end comes in contact with the ocular surface of the subject. Furthermore, the at least one capillary tube significantly reduces contact of the drug with the external environment, thereby eliminating chances of contamination of the drug. In an instance, the probe comprises multiple capillary tubes inside at least the first part of the probe. Optionally, the drug may be filled in the at least one capillary tube during manufacturing of the probe, and the probe is provided in a ready-to-use packaging to the user administering the drug.

Optionally, the at least one capillary tube is arranged to extend through the second part of the probe. Notably, in such instance, the at least one capillary tube is able to store a higher quantity of drug that is to be administered to the subject. Specifically, the extension of the at least one capillary tube through the second part of the probe increases volume thereof. More optionally, the second part of the probe comprises a reservoir therein for storing the drug, wherein the reservoir supplies drug to the at least one capillary tube. Beneficially, such storage of multiple doses of drug in the probe allows reuse of the probe, thereby enabling the probe to be cost-effective and reducing biomedical waste from single-use products.

Optionally, an amount of the drug administered onto the ocular surface in a single touch of the probe from the at least one capillary tube is based on a diameter of the capillary tube. Notably, a capillary tube with a larger diameter administers a greater amount of drug onto the ocular surface in comparison with a capillary tube of a smaller diameter. Therefore, a probe may be selected based on the diameter of the at least one capillary tube thereof to suit an amount of drug required to be administered to the subject.

Optionally, the first part of the probe is porous. Notably, the first part being porous allows adsorption and/or absorption of the drug thereon. Herein, the first part of the probe is immersed in a container of drug, wherein upon immersion the first part of the probe adsorbs and/or absorbs the drug. In an instance when the drug is in a powdered form, the first part of the probe adsorbs the powder thereon. Subsequently, the drug in the powdered form is administered from the distal end upon contact with the ocular surface. In another instance when the drug is a liquid form, the first part of the probe absorbs the liquid upon immersion in the container of drug. In an instance, the drug is adsorbed and/or absorbed on the first part of the probe during the manufacturing process of the probe. In another instance, the probe is immersed in the container of drug by the user prior to administering the drug.

In an embodiment, the first part of the probe comprises a concave cavity for carrying the drug. Specifically, the concave cavity is provided on the distal end of the first part of the probe. Therefore, the drug is administered on the ocular surface of the subject from the concave cavity provided at the distal end.

Pursuant to embodiments of the present disclosure, the probe touches the ocular surface gently. Notably, the probe contacts the ocular surface for a very momentary and brief period to ensure the safety of the eye and not cause any irritation or physical injury to the ocular surface. In this regard, the probe has sufficiently large surface area to prevent piercing through the ocular surface, thereby eliminating an instance of damage of tissues of the ocular surface.

The probe holding means is operable to hold the probe within the apparatus. The probe holding means retains the probe in its resting position and prevents the probe from dropping off of the apparatus. The probe holding means is strategically designed to allow movement of the probe along a longitudinal axis of the probe when in operation.

Optionally, the probe holding means comprises at least one magnetic coil, wherein the at least one magnet coil, when activated, applies a magnetic force on the second part of the probe and holds the second part of the probe within the probe holding means. Optionally, the at least one magnetic coil is placed inside the apparatus such that the at least one magnetic coil surrounds the probe. The at least one magnetic coil is configured to hold the probe in its initial position (or prevent the probe from dropping off of the apparatus). Moreover, the at least one magnetic coil is configured to be electrically controlled. Specifically, supplying electrical current to the at least one magnetic coil enables the at least one magnetic coil to produce a magnetic force. Such magnetic force enables the probe holding means to securely hold the probe within it using the second part of the probe, for example during measurements in horizontal as well as at an inclination with respect to the ocular surface of the subject. Notably, the probe can be easily detached from the apparatus by turning off the supply of electrical current to the at least one magnetic coil. It will be appreciated that the regulation of electrical current in the probe holding means assists in retention of the probe within the apparatus. Optionally, the at least one magnetic coil is arranged within a coil frame, wherein the coil frame is a skeleton structure that holds the at least one magnetic coil in a desired manner. Alternatively, optionally, the probe holding means comprises a mechanical lock, a frictional brake, an induction coil, an electrical conductor (for example, a wire) in shape of a coil, spiral, helix and the like. Additionally, or alternatively, optionally, the probe holding means induces an electric field, a frictional force and/or a magnetic field into the probe for its retention in the apparatus.

The apparatus comprises an induction coil and its control circuit. Notably, the control circuit is operable to control the induction coil to produce a first magnetic force and a second magnetic force, in an alternating manner, to release the probe in a first direction and to retract the probe in a second direction, respectively. Herein, when released in the first direction, the probe is to administer the drug from the distal end of the first part upon touching the ocular surface of the subject. The control circuit is operable to control a supply of electrical current flown through the induction coil. Such electrical current produces the first magnetic force that nullifies a force exerted by the probe holding means to retain the prove within the apparatus. It is to be understood that the speed of the probe is controlled by the flow of electrical current in the induction coil. Specifically, a higher electrical current in the induction coil results in a higher speed at which the probe is released from the probe holding means. Similarly, a lower electrical current in the induction coil results in a lower speed at which the probe is released from the apparatus. The control circuit further controls introduction of an electrical current opposite to the direction of the electrical current in the induction coil that led to release of the probe from the apparatus, in order to retract the probe, in the second direction, back into the apparatus. The induction coil and the control circuit can be understood to be "driving electronics" for the probe in the apparatus, namely for driving the movement of the probe. Optionally, the control circuit is implemented as hardware, software, firmware, or a combination of these. The control circuit is coupled to electrical current supply and the induction coil. Herein, the supply of the electrical current to the induction coil and its control circuit is provided from, for example, an electrical socket, at least one electrical battery, and the like. Optionally, the apparatus comprises a button thereon, wherein the button is employed to trigger the functioning of the control circuit.

Optionally, the apparatus further comprises:
  means for measuring an intraocular pressure of the eye;
  a controller configured to determine a total amount of the drug to be administered onto the ocular surface based on the measured intraocular pressure of the eye.

Optionally, in this regard, the means for measuring the intraocular pressure of the eye measures fluid pressure inside the eye of the subject. Notably, an increase in a value of intraocular pressure is indicative of the subject suffering from medical conditions such as glaucoma. One way for measuring the intraocular pressure may be implemented using rebound tonometry. The rebound tonometry is based on ejecting a probe towards ocular surface of the subject (for example surface of an eye of a person) and measuring one or more movement and impact parameters of the probe before, during and after impact of the probe with the ocular surface. In deed the apparatus which is suitable for measuring intraocular pressure comprises:
  a probe holding means for holding a probe within the apparatus, the probe comprising a first part and a second part, the first part being made of a bio-compatible material, the second part being made of a magnetic material, the first part having a proximal end connected to the second part and a distal end opposite to the proximal end, wherein the distal end of the first part is employed to carry the drug; and
  an induction coil and its control circuit, wherein the control circuit is operable to control the induction coil to produce a first magnetic force and a second magnetic force, in an alternating manner, to release the probe in a first direction and to retract the probe in a second direction, respectively and
the control circuit further configured to measure induced current in the induction coil during release and retract cycle. Changes of speed and accelerations of the probe during the cycle (and in particular during impact of the probe with ocular surface (eye surface o the user) can be used to determine intraocular pressure of the eye.

Optionally, the controller of the apparatus (or control circuit) comprises programmable components configured to store, process, and share information. For example, the controller may comprise at least one of: a network adapter, a memory unit, a processor. Pursuant to embodiments of the present disclosure, the controller governs operation of the components of the apparatus, namely, the probe holding means, the induction coil and its control circuit. Herein, in communication with the means for measuring the intraocular pressure of the eye, the controller uses the measurement of change in speed, acceleration of the probe to determine the intraocular pressure. Notably, the total amount of drug to be administered is dependent on the intraocular pressure indicative of the severity of the medical condition. In an instance, the controller stores information relating to the total amount of drug to be administered onto the ocular surface corresponding to different intraocular pressures. In another instance, the controller is communicably coupled to a database arrangement, wherein the controller is configured to obtain information relating to the total amount of drug to be administered from the database arrangement based on the measured intraocular pressure of the eye.

It will be appreciated that the total amount of the drug to be administered onto the ocular surface may change over a period of time based on an improving or worsening condition of the disease of the subject. Therefore, the means for measuring the intraocular pressure of the eye is configured to measure the intraocular pressure from the surface of the at regular intervals of time. Based on such measured intraocular pressure of the eye, the controller may increase or decrease the total amount of drug to be administered. Beneficially, such operation of the means for measuring the intraocular pressure and the controller substantially reduces or eliminates a need for regular eye check-ups that are performed by medical professionals to regulate the amount of drug required by a subject. Furthermore, the controller may store a temporal record of measurements of the intraocular pressure and may display such temporal record on the display of the apparatus, upon receiving a request from the user. In an instance, when there is a significant variation in measurements of intraocular pressure over a short period of time, the controller may display an alert on the display prompting the user to consult a physician or an ophthalmologist or an optometrist.

Optionally, the apparatus comprises a display and a keypad. Notably, the display and the keypad provide an interface which enables the user of the apparatus to provide input to the controller. Herein the input may be, but is not limited to, the amount of the drug administered onto the ocular surface in a single touch of the probe, the total amount of the drug to be administered onto the ocular surface. Notably, the amount of the drug administered onto the ocular surface in a single touch of the probe may vary based on a type of probe used. Therefore, the controller may prompt the user, via the display, to provide such input relating to the amount of the drug administered onto the ocular surface in a single touch, after every insertion of the probe into the apparatus. In an instance, the controller, via the display, provides the measured value of intraocular pressure to user. Consequently, based on the measured value of the intraocular pressure, the user determines the total amount of the drug to be administered onto the ocular surface, and provides it as an input to the controller, using the display and the keypad.

Optionally, the apparatus further comprises a controller configured to determine a total number of times the probe is to touch the ocular surface, based on a total amount of the drug to be administered onto the ocular surface and an amount of the drug administered onto the ocular surface in a single touch of the probe. As mentioned previously, the controller is configured to determine a total amount of the drug to be administered onto the ocular surface based on the measured intraocular pressure of the eye. Alternatively, optionally, the controller receives the total amount of the drug to be administered onto the ocular surface as an input from the user. It will be appreciated that multiple touches of the distal end of the probe onto the ocular surface may be required to administer the total amount of drug that is required by the subject. In an example, the amount of the drug administered onto the ocular surface in a single touch of the probe may be 0.5 micrograms (μg). Herein, the total amount of drug that is required by the subject may be 2 micrograms (μg). Therefore, the probe is required to touch the ocular surface four times to administer the required 2 micrograms (μg) of drug onto the ocular surface of the subject.

Optionally, the means for measuring the intraocular pressure of the eye is configured to measure one or more parameters related to the eye. Such parameters include, but are not limited to, corneal thickness, corneal curvature, corneal hydration, corneal rigidity, corneal opacity, ocular motility.

The apparatus comprises also as discussed:
a first sensor that is to be employed to sense a displacement and/or velocity of the probe; and
a controller configured to:
collect, from the first sensor, sensor data indicative of the displacement and/or velocity of the probe as a function of time;
analyse the sensor data to detect whether or not the probe touched the ocular surface during a given instance of release of the probe in the first direction.

In this regard, the first sensor measures the velocity and/or displacement of the probe and records sensor data related thereto. In an instance, the first sensor is configured to measure a change in magnetic flux in the induction coil due to a movement of the probe towards the ocular surface. Further alternatively the apparatus might comprise separate measurement coil which is part of the first sensor. As mentioned previously, the induction coil exerts a first magnetic force to release the probe in the first direction. Subsequently, the probe is retracted in the second direction to restore the magnetic flux. Therefore, the first sensor measures the changes in the magnetic flux in the induction coil to determine the displacement and/or velocity of the probe. The change in the magnetic flux can be detected by measuring induced voltage in the induction or measurement coil. The induced voltage is indication which can be used to determine velocity of the probe. The first sensor is thus considered to be combination of coil (induction or measurement coil) and controller or control circuit which converts measured induced voltage to velocity values. This can be done for example look up table providing correlation of induced voltage and speed of the probe. Additionally, or alternatively, optionally, the first sensor may be implemented using a transducer, an accelerometer, a frequency sensor, laser surface velocimeter, a piezoelectric sensor.

The sensor data, recorded or sensed by the first sensor, provides information relating to the displacement of the probe and/or the velocity of the probe as a function of time, during multiple instances of release of the probe in the first direction to administer the drug onto the ocular surface. Indeed, controller collects from the first sensor the sensor data indicative of displacement and/or velocity of the probe as a function of time. This data is analysed to detect whether or not the probe touched the ocular surface during a given instance of release of the probe in the first direction. As an example accelerometer or velocity profile of touch to eyelid is different from touch to eye surface. Eyelid can be for example less elastic than the eye surface thus the acceleration/velocity profile might show lower acceleration during impact to eyelid than to eye surface. Notably, the probe undergoes a characteristic change in displacement or velocity upon touching the ocular surface of the subject. Herein, a change in displacement or velocity of probe that is not analogous to the characteristic change in displacement or velocity that occurs when the probe touches the ocular surface indicates that the probe did not touch the ocular surface and therefore, the drug was not administered. Specifically, in such instance, the probe may have touched an eyelid or eyelashes of the subject and may exhibit a change in displacement or velocity that is not concurrent with the characteristic change of velocity. Beneficially, the first sensor and the controller enable an accurate and precise administration of the amount of drug that is required by the subject.

Further optionally the controller is configured to determine a total number of times the probe attempted to administer the drug, a number of times the probe is detected to have touched the ocular surface, and the number of times the probe is detected to have not touched the ocular surface. The controller of the apparatus can be optionally thus configured to determine a number of times the probe is to be released in the first direction to administer a total amount of the drug, based on a total number of times the probe is to touch the ocular surface and a number of times the probe is detected to have not touched the ocular surface. Technical effect of this is that we can precisely determine amount of drug delivered to the surface.

In an example, the total amount of drug that to be administered onto the ocular surface may be 5 micrograms (μg), wherein the amount of the drug administered onto the ocular surface in a single touch of the probe may be 0.2 micrograms (μg). Therefore, the controller determines that the total number of times the probe is to touch the ocular surface is 25. Thereafter, the probe administers the drug onto the ocular surface by attempting 25 instances of release of probe in the first direction. Subsequently, the controller collects and analyses sensor data, from the first sensor, for each instance and determines the number of times the probe is detected to have not touched the ocular surface. In such example, the number of times the probe is detected to have not touched the ocular surface may be 6. Therefore, the controller is configured to determine a number of times the probe is to be released in the first direction to administer a total amount of the drug, based on a total number of times the probe is to touch the ocular surface and a number of times the probe is detected to have not touched the ocular surface. In other words, the controller is configured to determine an additional number of times the probe is to be released in the first direction to administer a remaining amount of the drug as the number of times the probe is detected to have not touched the ocular surface. Herein, in the above example, the number of times the probe is to be released in the first direction to administer the total amount of drug is 6. In other words, the probe is required to touch the ocular surface 6 more times to administer the remaining amount of drug that could not be administered due to unsuccessful attempts.

Optionally, the apparatus further comprises:
a second sensor that is to be employed to sense an acceleration of the probe; and
a controller configured to determine an amount of the drug administered from the distal end of the probe, based on the acceleration of the probe.

Optionally, in this regard, the second sensor is employed to sense an acceleration of the probe. In an instance, the second sensor is configured to measure a change in magnetic flux in the induction coil due to a movement of the probe towards the ocular surface. As mentioned previously, the induction coil exerts a first magnetic force to release the probe in the first direction. Subsequently, the probe is retracted in the second direction to restore the magnetic flux. Therefore, the second sensor measures the changes in the magnetic flux in the induction coil to sense the acceleration of the probe. Additionally, or alternatively, optionally, the second sensor may be implemented using a transducer, an accelerometer, a frequency sensor, laser surface velocimeter, a piezoelectric sensor. In an instance, the second sensor comprises an accelerometer. It will be appreciated that the acceleration of the probe is a function of the accelerative forces induced in response to the magnetic force exerted by the induction coil. In this regard, the second sensor employs the accelerometer to measure such accelerative forces to measure the acceleration of the probe. In another instance, the second sensor comprises a speed sensor. The speed sensor measures instantaneous speed of the probe. The speed of the probe is measured as a function of time, during movement of the probe towards the ocular surface, to determine the acceleration of the probe. In an embodiment, the first sensor is configured to perform the functionality of the second sensor.

Optionally from hardware point of view the second sensor can be same as the first sensor. Difference is in a way the captured data is analysed i.e. velocity as function of time can be converted to obtain acceleration values. In deed the first sensor can be employed to sense an acceleration of the probe alternatively or additionally to sensing displacement and/or velocity of the probe. In said optional embodiment the controller is configured to determine an amount of the drug administered from the distal end of the probe, based on the acceleration of the probe.

The second sensor (or optionally the first sensor or could be also referred as acceleration measurement sensor) is employed to sense an acceleration of the probe and provide information to the controller communicably coupled to the sensor. The controller is configured to analyse the information provided by the second sensor and detect a change in acceleration of the probe. Herein, the acceleration of the probe measured by the second sensor is employed to determine an amount of the drug that has been provided to the ocular surface by measuring a change in a mass of the probe between multiple movements of the probe. Notably, the force exerted by the induction coil is constant, therefore the acceleration of the probe during a given movement of the probe is proportional to and indicative of the mass of the probe during the given movement. Consequently, a change in acceleration of the probe between two subsequent movements is measured and is used to determine the change in the mass of the probe using Newton's second law of motion that provides the equation:

$$m = F/a$$

wherein 'F' is the force exerted on the probe, 'a' is the acceleration of the probe and 'm' is the mass of the probe. It will be appreciated that the change in mass of the probe is a result of reduction of amount of drug from the distal end of the probe upon administration of the drug onto the ocular surface. Consequently, mass of the drug that was administered onto the ocular surface is determined as the calculated reduced mass of the probe. Beneficially, such measurement of acceleration of the probe enables an accurate determination of amount of drug administered onto the ocular surface after each actuation and consequently, enables the user to ensure a proper functioning of the probe.

Optionally, the apparatus further comprises a protrusion on an outer surface of the apparatus, wherein the protrusion enables to maintain a predefined separation between the first part of the probe and the ocular surface of the subject. During operation, such protrusion may rest on forehead of the subject, ensuring safety of the eye prior to administration of drug from the probe. Furthermore, the protrusion is configured to allow safe and friction-free retraction of the probe into the apparatus. Optionally, the predefined separation of the first part of the probe from the ocular surface lies in a range of 4 mm to 10 mm.

Optionally, the apparatus comprises an inserter employed to install the probe within the probe holding means. Herein, the inserter is a gripper-like structure that encloses the probe to allow a safe pickup of the probe and insertion of the probe into the probe holding means without damaging or contaminating the probe. Furthermore, the probe may be packed in a probe tube that is placed in packaging of the probe. Herein, the probe tube is opened (for example, by removing a cap thereof) under hygienic conditions to access the probe. Optionally, the inserter is implemented as a probe base cover. The probe base cover is strategically designed to receive the probe from the probe tube and insert the probe into the apparatus. In an instance, the probe base cover is made of a substantially transparent and flexible material. Herein, the probe base cover may be squeezed to create a suction pressure to pick up the probe from the probe tube and to release during the placement of the probe into the apparatus.

Optionally, the apparatus comprises a housing. Herein, the term "housing" refers to a protective covering that substantially encases components, namely, the probe holding means, the induction coil and its control circuit, and the probe. Notably, the housing has an interior and exterior portion. Optionally, the housing has a tubular form-factor. Alternatively, the housing comprises any form-factor selected from any of: an elliptical, a cylindrical, a cuboidal, a conical or any other polygonal form-factor. In an instance, the housing is manufactured using a polymer. In another instance, the housing is manufactured using a metal alloy.

Optionally, the apparatus further comprises an attachment means for holding a cartridge. Herein, the cartridge refers to a container holding one or more doses of drug therein. The attachment means is configured to receive and hold a cartridge therein, wherein when received the attachment means enables fluidic coupling between the cartridge and the probe. More optionally, the attachment means enables fluidic coupling between the cartridge and at least one capillary tube extending through the second part of the probe. Such fluidic coupling allows a supply of drug from the cartridge to the at least one capillary tube and subsequently, to the distal end of the first part of the probe. Optionally, the apparatus comprises the cartridge.

The present disclosure also relates to the system as described above. Various embodiments and variants disclosed above apply mutatis mutandis to the system.

Optionally, the system comprises a computing device communicably coupled to the apparatus. Herein, the term "computing device" refers to an electronic device associated with (or used by) a user that is capable of enabling the user to perform specific tasks associated with the aforementioned apparatus. Examples of computing devices include, but are not limited to, cellular phones, personal digital assistants (PDAs), handheld devices, laptop computers, personal computers, etc. The computing device is intended to be broadly interpreted to include any electronic device that may be used for data communication with the apparatus over a wired or wireless communication network. Such data communication networks include, but are not limited to, Local Area Networks (LANs), Wide Area Networks (WANs), Metropolitan Area Networks (MANs), the Internet, radio networks (for example, such as Bluetooth®), telecommunication networks. Optionally, the computing device is implemented as an input device to provide inputs to the apparatus and specifically, the controller. Herein, the input may be, but is not limited to, the amount of the drug administered onto the ocular surface in a single touch of the probe, the total amount of the drug to be administered onto the ocular surface. Furthermore, the apparatus provides information relating to operation of the apparatus to the computing device, wherein such information is to be presented to the user via the display of the computing device. Such information may include, but is not limited to, measured intraocular pressure, one or more notifications communicating a successful administration of the drug.

DETAILED DESCRIPTION OF THE DRAWINGS

Figure 1:
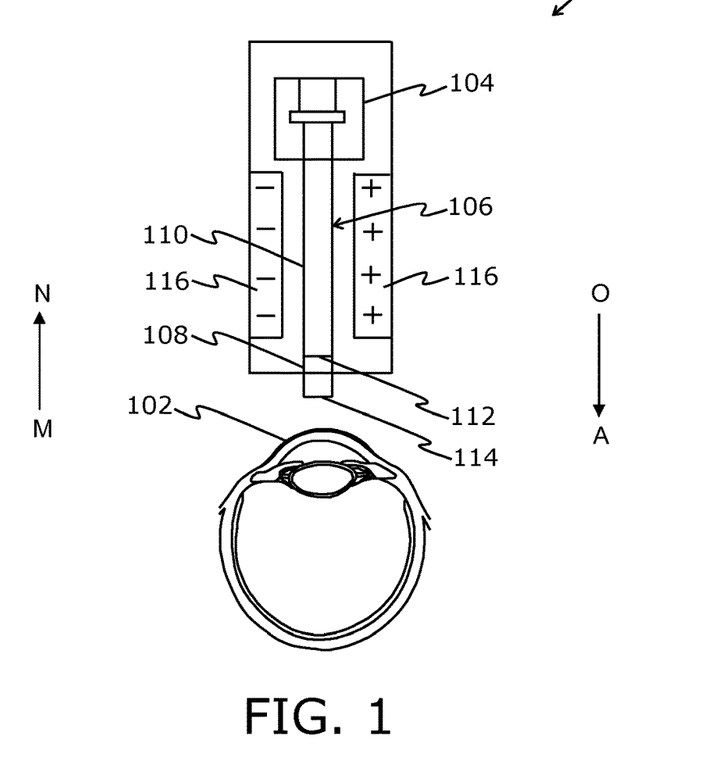
FIG. 1 is a schematic illustration of an apparatus for administering a drug onto an ocular surface of a subject, in accordance with an embodiment of the present disclosure.

Referring to FIG. 1, illustrated is a schematic illustration of an apparatus 100 for administering a drug onto an ocular surface 102 of a subject, in accordance with an embodiment of the present disclosure. As shown, the apparatus 100 comprises a probe holding means 104 for holding a probe 106 within the apparatus 100. The probe 106 comprises a first part 108 and a second part 110, the first part 108 being made of a bio-compatible material, the second part 110 being made of a magnetic material. The first part 108 has a proximal end 112 connected to the second part 110 and a distal end 114 opposite to the proximal end 112, wherein the distal end 114 of the first part 108 is employed to carry the drug. The apparatus 100 comprises an induction coil 116 and its control circuit (not shown). The control circuit is operable to control the induction coil 116 to produce a first magnetic force and a second magnetic force, in an alternating manner, to release the probe 106 in a first direction as indicated by arrow O-A and to retract the probe 106 in a second direction as indicated by arrow M-N, respectively. When released in the first direction as indicated by arrow O-A, the probe 106 is to administer the drug from the distal end 114 of the first part 108 upon touching the ocular surface 102 of the subject.

Figure 2:
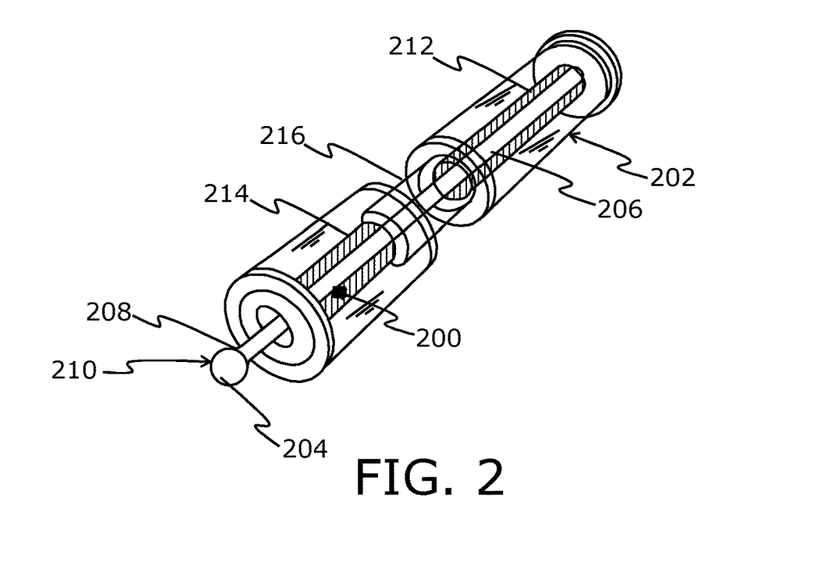
FIG. 2 is an illustration of a probe arranged within an apparatus, in accordance with an embodiment of the present disclosure.

Referring to FIG. 2, there is shown an illustration of a probe 200 arranged within an apparatus 202, in accordance with an embodiment of the present disclosure. As shown, the probe 200 is implemented as an elongate instrument having a first part 204 and a second part 206, wherein the first part 204 of the probe is implemented as a spherical or ellipsoidal element. The first part 204 has a proximal end 208 and a distal end 210 diametrically opposite to the proximal end 208. The distal end 210 of the first part 204 is employed to carry the drug. The probe 200 is detachably arranged within the apparatus 202. The probe 200 is held within the apparatus 202 by a probe holding means 212. Herein, an induction coil 214 is operable to release the probe 200 towards the ocular surface and to retract the probe 200 into the apparatus 202. A control circuit 216 is operable to control the induction coil 214 to produce a first magnetic force and a second magnetic force, in an alternating manner, to release the probe 200 in a first direction and to retract the probe 200 in the second direction, respectively.

Figure 3A:
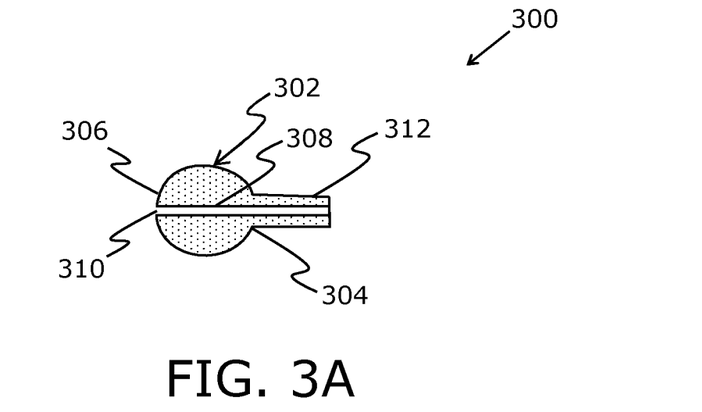
FIGS. 3A, 3B and 3C are schematic illustrations of a probe, in accordance with various embodiments of the present disclosure.
Figure 3B:
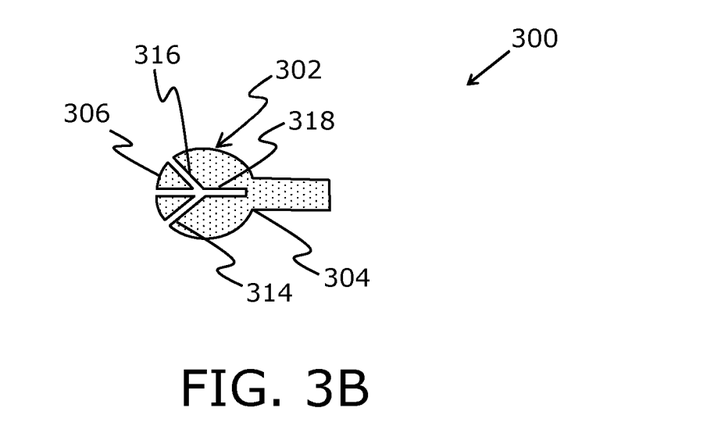
Figure 3C:
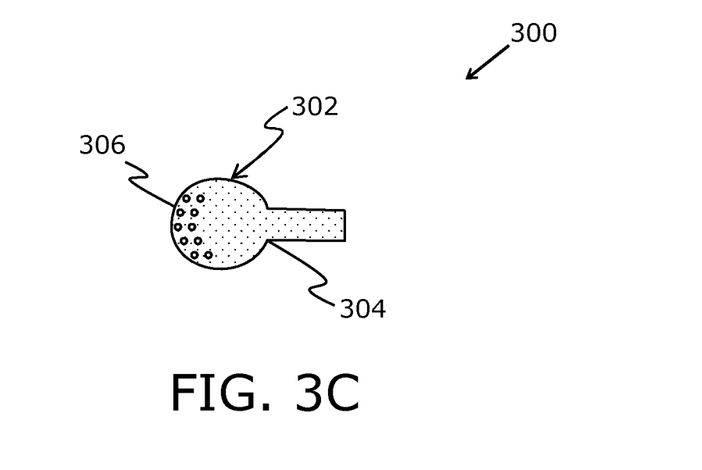

Referring to FIGS. 3A, 3B and 3C, illustrated are schematic illustrations of probe 300, in accordance with various embodiments of the present disclosure. As shown, the probe 300 is implemented as an elongate instrument, wherein the first part 302 of the probe is implemented as a spherical or ellipsoidal element. The first part 302 has a proximal end 304 and a distal end 306 diametrically opposite to the proximal end 304.

As shown in FIG. 3A, the probe 300 comprises a capillary tube 308. The capillary tube 308 is filled with drug. The capillary tube 308 is arranged inside the first part 302 and extends through a second part 312 of the probe 300. An opening 310 of the capillary tube 310 is provided at the distal end 306 to administer the drug onto the ocular surface.

As shown in FIG. 3B, the probe 300 comprises multiple capillary tubes, such as the capillary tubes 314, 316 and 318. The multiple capillary tubes 314, 316 and 318 are arranged inside the first part 302 of the probe 300.

As shown in FIG. 3C, the first part 302 of the probe 300 is porous. The first part 302 being porous allows adsorption and/or absorption of the drug thereon to be administered from the distal end 306 of the first part 302.

Figure 4:
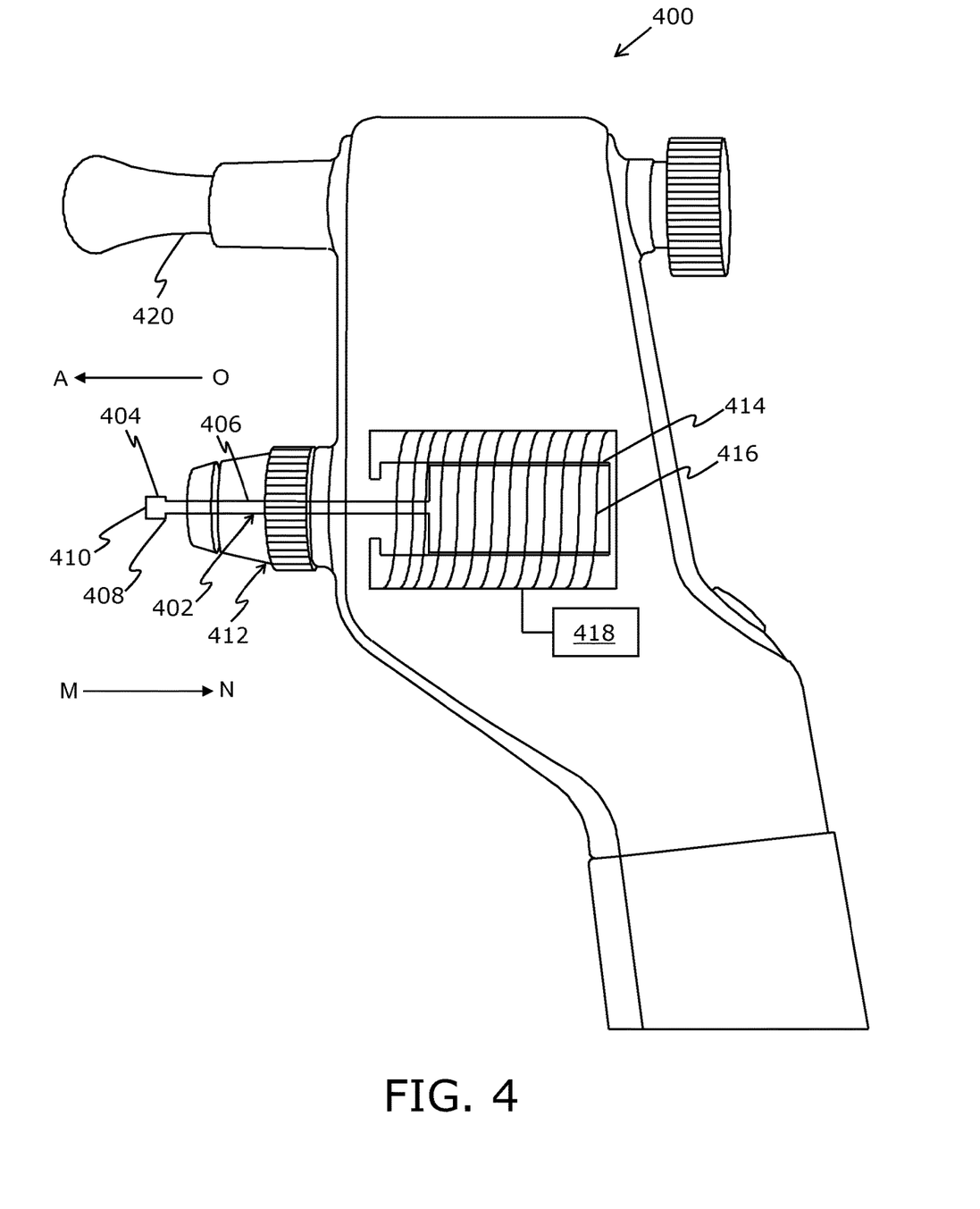
FIG. 4 is a schematic illustration of a system for administering a drug onto an ocular surface of a subject, in accordance with an embodiment of the present disclosure.

Referring to FIG. 4, illustrated is a schematic illustration of a system 400 for administering a drug onto an ocular surface of a subject, in accordance with an embodiment of the present disclosure. The system 400 comprises a probe 402 (such as the probe 106 of FIG. 1) comprising a first part 404 and a second part 406. The first part 404 has a proximal end 408 and a distal end 410 opposite to the proximal end 408, wherein the distal end 410 of the first part 404 is employed to carry the drug. The system 400 also comprises an apparatus 412 (similar to the apparatus 100 of FIG. 1). The apparatus 412 comprises a probe holding means 414 for holding the probe 402 within the apparatus 412, and an induction coil 416 and its control circuit 418. The control circuit 418 is operable to control the induction coil 416 to produce a first magnetic force and a second magnetic force, in an alternating manner, to release the probe 402 in a first direction as indicated by arrow O-A and to retract the probe 404 in a second direction as indicated by arrow M-N, respectively. When released in the first direction as indicated by arrow O-A, the probe 402 is to administer the drug from the distal end 410 of the first part 404 upon touching the ocular surface (not shown) of the subject. The apparatus 412 further comprises a protrusion 420 on an outer surface of the apparatus 412. The protrusion 420 enables to maintain a predefined separation between the first part 404 of the probe 402 and the ocular surface of the subject.

Figure 5A:
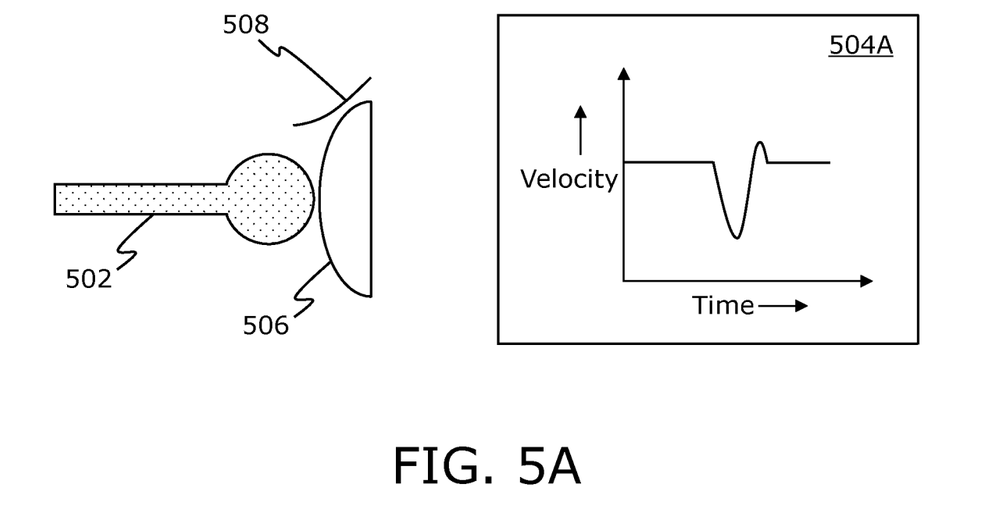
FIGS. 5A and 5B are schematic illustrations of operation of a probe corresponding to graphical representations of sensor data indicative of velocity of the probe as a function of time during the operation of the probe, in accordance with an embodiment of the present disclosure.
Figure 5B:
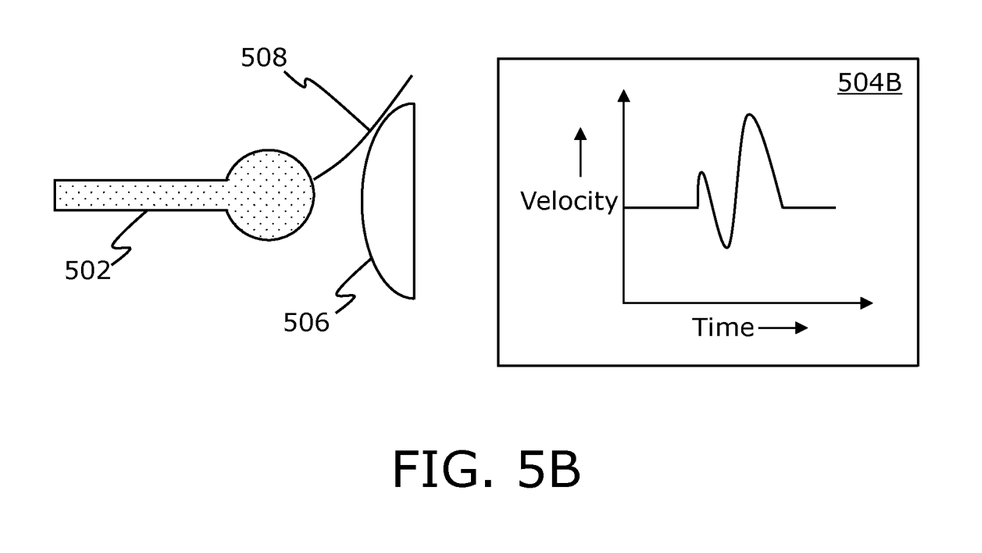

Referring to FIGS. 5A and 5B, there are shown schematic illustrations of operation of a probe 502 corresponding to graphical representations of sensor data indicative of velocity of the probe 502 as a function of time during the operation of the probe 502, in accordance with an embodiment of the present disclosure. Herein, the sensor data is received from a first sensor. Notably, the sensor data represented as graphical representations 504A and 504B is sensed during two different instances of release of probe 502 in a first direction (such as the first direction indicated by arrow O-A in FIG. 1).

As shown in FIG. 5A, the sensor data represented as graphical representation 504A is sensed during an instance when the probe 502 released in the first direction touches the ocular surface 506 of the subject and is not obstructed by an obstruction 508, such as an eyelid or eyelashes of the subject. In FIG. 5B, the sensor data represented as graphical representation 504B is sensed during an instance when the probe 502 is obstructed by the obstruction 508 and does not touch the ocular surface 506 of the subject. Notably, the graphical representation 504A illustrates a characteristic change in velocity that the probe 502 experiences upon touching the ocular surface 506 of the subject. Herein, the graphical representation 504B illustrates a change in velocity of probe 502 that is not analogous to the characteristic change in velocity that occurs when the probe 502 touches the ocular surface, as illustrated by the graphical representation 504A. Therefore, the graphical representation 504A indicates a successful administration of drug onto the ocular surface 506, whereas the graphical representation 504B indicates an unsuccessful attempt at administration of drug.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An apparatus for administering a drug onto an ocular surface of a subject, the apparatus comprising:
   a probe;
   a probe holding means for holding the probe within the apparatus,
   the probe comprising:
      a first part being made of a bio-compatible material, and
      a second part being made of a magnetic material,
      the first part having a proximal end connected to the second part and a distal end opposite to the proximal end, wherein the distal end of the first part is employed to carry the drug; and
   an induction coil and its control circuit, wherein the control circuit is configured to control the induction coil to produce a first magnetic force and a second magnetic force, in an alternating manner, to release the probe in a first direction and to retract the probe in a second direction, respectively, wherein, when released in the first direction, the probe is to administer the drug from the distal end of the first part upon touching the ocular surface of the subject;
   a first sensor that is to be employed to sense a displacement and/or velocity of the probe; and
   a controller configured to:
      collect, from the first sensor, sensor data indicative of the displacement and/or velocity of the probe as a function of time;
      analyse the sensor data to detect whether or not the probe touched the ocular surface during a given instance of release of the probe in the first direction, wherein the probe undergoes a characteristic change in displacement or velocity upon touching the ocular surface of the subject, and wherein a change in displacement or velocity of the probe that is not analogous to the characteristic change in displacement or velocity indicates that the probe did touch a surface that is not the ocular surface of the subject;
      determine a number of times the probe is to be released in the first direction to administer a total amount of the drug, based on a total number of times the probe is to touch the ocular surface, a number of times the probe is detected to have touched a surface that is not the ocular surface.

2. The apparatus according to claim 1, wherein the probe further comprises at least one capillary tube arranged inside at least the first part of the probe, an opening of the at least one capillary tube being at the distal end of the first part, the at least one capillary tube being filled with the drug.

3. The apparatus according to claim 1, further comprising:
   means for measuring an intraocular pressure of the eye;
   means for storing information relating to a total amount of drug to be administered onto the ocular surface corresponding to different intraocular pressures, or obtain information relating to the total amount of drug to be administered from a database arrangement based on the measured intraocular pressure of the eye; and
   the controller further configured to determine a total amount of the drug to be administered onto the ocular surface based on the measured intraocular pressure of the eye.

4. The apparatus according to claim 1, further comprising the controller further configured to determine a total number of times the probe is to touch the ocular surface, based on a total amount of the drug to be administered onto the ocular surface and an amount of the drug administered onto the ocular surface in a single touch of the probe.

5. The apparatus according to claim 1, further comprising:
   a second sensor that is to be employed to sense an acceleration of the probe; and
   the controller further configured to determine an amount of the drug administered from the distal end of the probe, based on the acceleration of the probe, wherein a change in acceleration of the probe between two subsequent movements is measured and used to determine a change in a mass of the probe, and wherein the amount of the drug that is administered is determined as the change in the mass of the probe.

6. A system for administering a drug onto an ocular surface of a subject, the system comprising:
   a probe comprising
      a first part being made of a bio-compatible material, and
      a second part being made of a magnetic material,
      the first part having a proximal end connected to the second part and a distal end opposite to the proximal end, wherein the distal end of the first part is employed to carry the drug; and
   an apparatus comprising:
      probe holding means for holding the probe within the apparatus; and
      an induction coil and its control circuit, wherein the control circuit is configured to control the induction coil to produce a first magnetic force and a second magnetic force, in an alternating manner, to release the probe in a first direction and to retract the probe in a second direction, respectively, wherein, when released in the first direction, the probe is to administer the drug from the distal end of the first part upon touching the ocular surface of the subject;
   at least one capillary tube arranged inside at least the first part of the probe, an opening of the at least one capillary tube being at the distal end of the first part, the at least one capillary tube being filled with the drug;
   a first sensor that is to be employed to sense one or more of a displacement and velocity of the probe; and
   a controller configured to:
      collect, from the first sensor, sensor data indicative of one or more of the displacement and velocity of the probe as a function of time;
      analyse the sensor data to detect whether or not the probe touched the ocular surface during a given instance of release of the probe in the first direction, wherein the probe undergoes a characteristic change in displacement or velocity upon touching the ocular surface of the subject, and wherein a change in displacement or velocity of the probe that is not analogous to the characteristic change in displacement or velocity indicates that the probe did touch a surface that is not the ocular surface of the subject.

7. The system according to claim 6, wherein the apparatus further comprises:
   means for measuring an intraocular pressure of the eye;
   storing information relating to a total amount of drug to be administered onto the ocular surface corresponding to different intraocular pressures, or obtaining information relating to the total amount of drug to be administered from a database arrangement based on the measured intraocular pressure of the eye; and
   the controller further configured to determine a total amount of the drug to be administered onto the ocular surface based on the measured intraocular pressure of the eye.

8. The system according to claim 6, wherein the apparatus further comprises the controller further configured to determine a total number of times the probe is to touch the ocular surface, based on a total amount of the drug to be administered onto the ocular surface and an amount of the drug administered onto the ocular surface in a single touch of the probe.

9. The system according to claim 6, wherein the apparatus further comprises:
   the controller further configured to determine a number of times the probe is to be released in the first direction to administer a total amount of the drug, based on a total number of times the probe is to touch the ocular surface and a number of times the probe is detected to have not touched the ocular surface.

\* \* \* \* \*